(12) United States Patent
Zhao et al.

(10) Patent No.: US 9,439,934 B1
(45) Date of Patent: Sep. 13, 2016

(54) **APPLICATION OF AN ATTENUATED *SALMONELLA TYPHIMURIUM*, ITS GENETICALLY ENGINEERED BACTERIUM IN PREPARING DRUGS FOR THE TREATMENT OF PROSTATE CANCER**

(71) Applicant: NANJING SINOGEN BIOTECH & PHARMACEUTICAL INC., Nanjing, Jiangsu (CN)

(72) Inventors: Allan Zijian Zhao, Jiangsu (CN); Sujin Zhou, Jiangsu (CN); Yan Lin, Jiangsu (CN); Zhenggang Zhao, Jiangsu (CN); Fanghong Li, Jiangsu (CN)

(73) Assignee: NANJING SINOGEN BIOTECH & PHARMACEUTICAL INC., Nanjing, Jiangsu (CN)

( * ) Notice: Subject to any disclaimer, the term of this patent is extended or adjusted under 35 U.S.C. 154(b) by 0 days.

(21) Appl. No.: 14/813,338

(22) Filed: Jul. 30, 2015

(51) Int. Cl.
| | |
|---|---|
| *C12N 15/74* | (2006.01) |
| *C12N 9/88* | (2006.01) |
| *A61K 35/74* | (2015.01) |
| *A61K 35/00* | (2006.01) |

(52) U.S. Cl.
CPC .............. *A61K 35/74* (2013.01); *C12N 15/74* (2013.01); *A61K 2035/11* (2013.01)

(58) Field of Classification Search
CPC .. A61K 38/00; A61K 48/005; C07K 14/195; C12N 15/74; C12N 9/88
See application file for complete search history.

(56) References Cited

PUBLICATIONS

Hum Gene Ther. 2001, 12(12):1594-6.*
The Journal of Infectious Diseases 2000;181:1996-2002.*
Acta Biochimica Polonica 2013, vol. 60, No. 3, 285-297.*
Oncology Research 2001, vol. 12, pp. 501-508.*

* cited by examiner

*Primary Examiner* — Padma V Baskar
(74) *Attorney, Agent, or Firm* — Rankin, Hill & Clark LLP

(57) ABSTRACT

The current invention discloses an attenuated *Salmonella typhimurium*, a genetically engineered bacterium and applications thereof in preparing drugs for the treatment of prostate cancer. The attenuated *Salmonella typhimurium* has tumor targeting and significant inhibitory effects on prostate cancer cells. A genetically engineered bacterium bearing a L-methioninase gene plasmid also has tumor targeting ability. The attenuated *Salmonella typhimurium* with the plasmid can constitutively express L-methioninase in the tumor tissues, consume a significant amount of methionine and other nutrients, which in turn causes lack of nutrition and slow growth of tumor cells. Therefore, it can be used as drugs for treating prostate cancer.

5 Claims, 7 Drawing Sheets

APPLICATION OF AN ATTENUATED *SALMONELLA TYPHIMURIUM*, ITS GENETICALLY ENGINEERED BACTERIUM IN PREPARING DRUGS FOR THE TREATMENT OF PROSTATE CANCER

TECHNICAL FIELD

The current invention relates to pharmaceutical technical field, in particular, to the applications of attenuated *Salmonella typhimurium*, which includes genetically engineered bacterium in preparing the drugs for the treatment of prostate cancer.

BACKGROUND OF THE INVENTION

Prostate cancer is the most common malignancy in men in European and the US. Its incidence is in the first place among all male malignancies in the US, and its mortality is only second to lung cancer. In recent years, its incidence is on the rise every year in China. In addition, the histological malignancy of prostate cancer in the Chinese patients is higher than in the patients of the US. According to the survey on the survival of patients with urinary tract cancer in Shanghai, China, 80-90% of the prostate cancer patients in China are advanced prostate cancer when diagnosed and their 5-year survival rate is lower than 30%. Considering the large population of China and the number of patients with prostate cancer is surging, it is necessary to focus on the prevention and better treatment of prostate cancer. Traditional prostate cancer treatment methods include surgery, endocrine therapy, chemotherapy, and radiation therapy, and the outcome still remains to be improved. The recurrence rate after surgery is relatively high. For recurrent prostate cancer, the endocrine therapy of androgen deprivation is often necessary. The endocrine therapy of prostate cancer can be divided into three categories: castration therapy, anti-androgen therapy, and a combination of both. After the endocrine therapy continues 2-5 years, prostate cancer will often develop to become androgen-independent. For androgen-independent patients with prostate cancer, the current therapies include chemotherapy, radiotherapy, radionuclide irradiation and bisphosphonate therapy, etc, all of which are of limited effect. The treatment of prostate cancer needs improvement and it is urgent to seek a more effective therapeutic regimen. Thus, scientists and clinical experts are actively exploring relatively safe and effective therapeutic regimens. With the advances in bacterial- and viral-based gene therapy and genetic engineering technology, mounting studies have focused on bacterial treatment of tumors. Since mid-1990s, studies have found that attenuated *Salmonella typhimurium* can kill the tumor cells effectively in mice.

*Salmonella* is a group of Gram-negative, invasive intracellular facultative anaerobes parasitized in human and animal intestinal tracts. VNP20009 is an attenuated *Salmonella typhimurium* strain with deletion of msbB and pur I genes. It is genetically stable and sensitive to antibiotics. The msbB protein is necessary for the lipid acylation to endotoxin, and the lipid acylation at A-terminal cannot be achieved when deletion, lowering the toxicity. The pur I protein is involved in purine metabolism, deletion of this gene leads to dependence of exogenous adenine when culturing the bacteria. These gene manipulations of VNP20009 also lower the production of tumor necrosis factor (TNF), thereby reducing inflammatory response. Consequently, the low pathogenicity improves the safety of its clinical usage. VNP20009 has been widely used in cancer research, which can influence the growth of a variety of solid tumor models of mice, including melanoma, lung cancer, colon cancer, breast cancer, and renal cancer. VNP20009, as a vector of gene therapy, has the ability to accumulate in the tumor site in a highly targeted fashion. Researchers have found in the mouse models carrying a variety of solid tumors that the quantity of VNP20009 in tumors is 200-1000 times as high as that in non-cancerous major organs, such as the liver. VNP20009 can preferentially accumulate and multiply under the hypoxic and necrotic conditions in the tumor tissue. At the same time, the bacterial multiplies significantly faster in the tumor tissues than in the normal tissues, making it possible for the attenuated *Salmonella* to be a new type of anti-tumor agent and the vector of targeted gene therapy. Potential mechanisms for the effect of a slow tumor growth by VNP20009 may include the follows: 1) Breakdown of nutrients necessary for tumor growth by the bacteria (e.g., through the enzymes produced by bacteria such as asparaginase) can deplete essential amino acids for tumor growth; 2) Stimulation of local toxin secretion or tumor necrosis factor α to tumor microenvironment can negatively influence the tumor angiogenesis. In addition, the non-specific inflammatory reaction at the bacterial growth site can activate anti-tumor T cells. However, so far, the antitumor activity of VNP20009 on prostate cancer cells has not been revealed.

In order to maintain its high rate of reproduction, tumor cells require adequate nutrition. In addition to carbohydrates, the need for methionine (Met), glutamine, and arginine is particularly high. Previous studies have established that Met-dependency is a common feature of most tumor cells, such as breast cancer, prostate cancer, lung cancer, colon cancer, kidney cancer, bladder cancer, melanoma, glioma, etc. High Met-dependency does not exist in normal cells. Both in vivo and in vitro experiments have confirmed that dietary intervention with methionine deficiency can delay the proliferation of tumor cells. However, long-term deficiency of Met can cause malnutrition, metabolic disorders, and aggravate tumor growth due to a long-term DNA hypomethylation. Thus, by specifically degrading Met through L-methioninase and lowering the level of methionine in vivo, we will be able to effectively inhibit the growth of tumor cells or even degrade them. Experiments in animal models have confirmed that intraperitoneal injection of methioninase can inhibit the growth of Yoshida sarcoma and lung tumor in nude mice. In previous clinical trials, four patients with breast cancer, lung cancer, kidney cancer and lymphoma received methioninase injection once every 24 h. Methioninase could significantly reduce the methionine content in plasma. However, since methioninase is not natively expressed in mammalians, exogenous administration has strong side effects often related to immunological response.

SUMMARY OF THE INVENTION

A technical problem to be solved in the current invention is to describe the applications of attenuated *Salmonella typhimurium* and its genetically engineered bacterium in the preparation of biological drugs for the treatment of prostate cancer.

To reach such goal, the current invention deployed the technical schemes as follows:

This invention provides the applications of attenuated *Salmonella typhimurium* in preparing drugs for the treatment of prostate cancer, and the said attenuated *Salmonella typhimurium* is VNP20009.

This invention also provides the applications of a genetically engineered bacterium in preparing drugs for the treatment of prostate cancer, and the said genetically engineered bacterium is a recombinant attenuated *Salmonella typhimurium* VNP20009 carrying a specific plasmid.

Wherein, the said plasmid is pSVSPORT plasmid, pTrc99A plasmid, pcDNA3.1 plasmid, pBR322 plasmid or pET23a plasmid. The said plasmid is transformed into attenuated *Salmonella typhimurium* VNP20009 by electroporation. The said electroporation condition is as follows: voltage 2400V, resistance 400Ω, capacitance 25 µF, discharge time 4 ms.

This invention also provides the applications of a genetically engineered bacterium in preparing drugs for the treatment of prostate cancer, wherein the said genetically engineered bacterium is a recombinant attenuated *Salmonella typhimurium* VNP20009 carrying a plasmid, and a L-methioninase gene is cloned into the said plasmid.

Wherein, the said plasmid is pSVSPORT plasmid, pTrc99A plasmid, pcDNA3.1 plasmid, pBR322 plasmid, and pET23a plasmid. The procedures for the construction of the said genetically engineered bacterium are as follows: the L-methioninase gene is subcloned into the plasmid to obtain L-methioninase expressing plasmid. The L-methioninase expressing plasmid is transformed into attenuated *Salmonella typhimurium*, VNP20009, to obtain the genetically engineered bacterium. The said electroporation condition is as follows: voltage 2400V, resistance 400Ω, capacitance 25 µF, discharge time 4 ms.

Preferably, when pSVSPORT plasmid is used in the construction of genetically engineered bacterium, the L-methioninase gene is subcloned into the plasmid through the Kpn I and Hind III restriction sites to obtain L-methioninase expression plasmid, which then is transformed into attenuated *Salmonella typhimurium*, VNP20009, to obtain the genetically engineered bacterium.

The route of administration of the above attenuated *Salmonella typhimurium* and its genetically engineered bacterium is intratumoral injection.

Therapeutic effects: the attenuated *Salmonella typhimurium* has tumor targeting and significant inhibitory effect on prostate cancer cells. The genetically engineered bacterium also has a tumor targeting effect. The attenuated *Salmonella typhimurium* with the cloned L-methioninase gene plasmid can continuously express L-methioninase in the tumor tissues, which then consumes methionine and a series of other nutrients, and depletes the tumor cells of nutrition, causing slow growth. Therefore, it can be used as the drug for the treatment of prostate cancer.

DETAILED DESCRIPTION OF THE EMBODIMENT

The invention is described herein in connection with drawings and certain specific embodiments. However, to the extent that the following detailed description is specific to a particular embodiment or a particular use, this is intended to be illustrative only and is not to be construed as limiting the scope of the invention.

Example 1

Construction of Genetically Engineered Bacterium (1) Construction of Plasmids Expressing L-Methioninase Gene Firstly, the L-methioninase (GenBank: L43133.1) is synthesized and subcloned into pUC57 plasmid (GenScript Corporation), then subcloned into plasmid pSVSPORT (Invitrogen) through Kpn I and Hind III restriction sites, to get pSVSPORT-L-methioninase expressing plasmid. The specific procedures are as follows:

Double enzyme digestion of plasmid pSVSPORT with Kpn I and Hind III: 2 µg plasmid DNA, 34, 10× buffer, 1.54 Kpn I, 1.5 µL Hind III. Add ddH$_2$O to 30 µL and incubate at 37° C. for 3 h, and then separate the digests by 1% agarose gel electrophoresis, to cut out DNA bands with the size of 4.1 kb, and then purify DNA using the gel recovery and purification kit.

The DNA fragments in L-methioninase coding region obtained by gene synthesis are subcloned into plasmid pUC57 (GenScript Corporation). Perform restriction digests as follows: 3 µg plasmid DNA, 34, 10× buffer, 1.54 Kpn I, 1.54 Hind III. Add ddH$_2$O to 30 µL and incubate at 37° C. for 3 h. Then separate the digests by 1% agarose gel electrophoresis. We cut out DNA bands with the size of 1.2 kb, and then purify DNA using a gel recovery and purification kit.

The pSVSPORT (Kpn I/Hind III) is ligated to DNA fragment of L-methioninase coding region (Kpn I/Hind III). Add 24, vector, 64, inserted fragment, 1 µL T4 DNA ligase in the ligation reaction, and incubate at 16° C. for 16 h.

The ligation product is transformed to competent cells of *E. coli* DH5α (Takara). Use one tube 50 µL of DH5α competent cells and place on ice until thawing. Add 5 µL of the above ligation product to the DH5α and mix them gently, and then incubate on ice for 30 min; after heat shock at 42° C. for 60 s, cold shock on ice for 2 min; add 500 µL of LB without antibiotic and culture at 37° C. with shaking for 1 h; spin tube at 4000 rpm for 5 min; remove all but 100 µL of LB and resuspend pellet with pipette tip. Place suspensions on LB plate containing ampicillin, and then incubate at 37° C. for 16 h.

Figure 1:
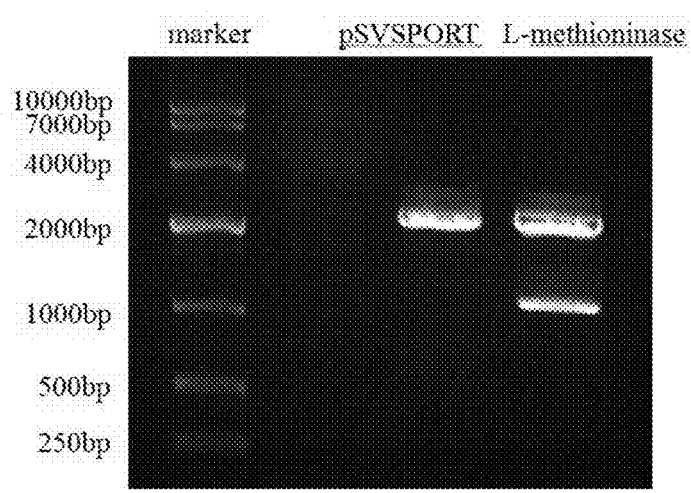
FIG. 1 shows 1% agarose gel electrophoresis by plasmid pSVSPORT-L-methioninase following restriction enzyme digestion.

When clones grow out, pick up the monoclonal colonies into 3 mL LB containing ampicillin, culture at 37° C. with shaking for 1 h. Extract the plasmid DNA from cultures and identify by Kpn I and Hind III restriction analysis. DNA bands of 4.1 and 1.2 kb are measured in positive clones, as shown in FIG. 1. Then the positive clone is sent for sequencing to confirm the identity of the insert fragment.

(2) Construct VNP20009 Carrying Vector and VNP20009-L-Methioninase Strain

The plasmid pSVSPORT and pSVSPORT-L-methioninase are electroporated into VNP20009 strain (YS1646, ATCC No. 202165), named VNP20009-V and VNP20009-M respectively. The specific construction procedures are as follows:

Place competent bacteria VNP20009 on ice. After thawing, transfer it to a pre-cooled electroporation cuvette and add 2¢ plasmid, slightly mix them, then incubate on ice for 1 min. Put the cuvette into electroporation apparatus set to 2400V, 400Ω, 25 µF and 4 ms. After pulse, immediately add 1 mL SOC medium to the cuvette and mix gently. Culture at 37° C. with shaking for 1 h, centrifuge at 4000 rpm for 5 min and remove all but 100¢ of LB and resuspend pellet with pipette tip. Plate the electroporation mixture on LB plate containing ampicillin, and then incubate at 37° C. for 16 h. After VNP20009-V and VNP20009-M are cultured with LB-O, extract the plasmid and identification by restriction digestion.

Figure 2:
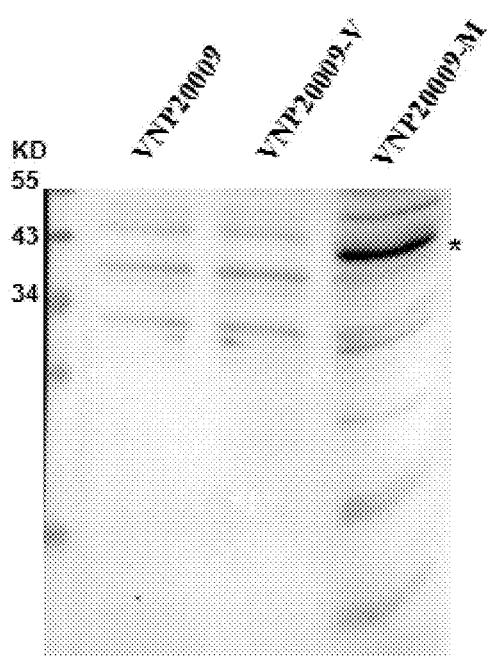
FIG. 2 shows methioninase expression identification by Western blot.

Extract proteins from $1 \times 10^8$ *Salmonella* and separate by 10% SDS-PAGE electrophoresis, transfer to PVDF membranes in an ice bath. The membranes are blocked by incubation in BSA at room temperature for 1 h. After three 5-min washes in TBST, the membranes are incubated at 4° C. overnight with rabbit antibody against L-methioninase (1:1000). After three 5-min washes in TBST, the membranes are incubated with horseradish peroxide-conjugated anti-rabbit secondary antibodies (1:10000) for 1 hr at room temperature. After three 5-min washes in TBST, the protein bands are visualized using enhanced chemiluminescence (ECL) reagents. The results are shown in FIG. 2. There is a specific band at about 43 kD molecular weight, suggesting compared with that of VNP20009 and VNP20009-V, L-methioninase expression of VNP20009-M is significantly increased.

Figure 3:
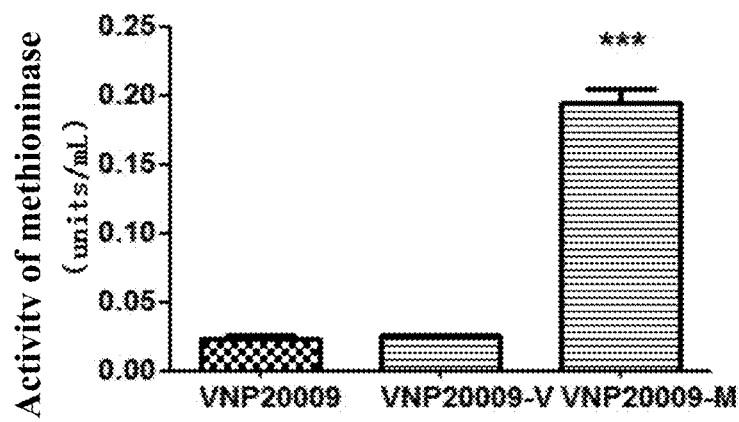
FIG. 3 shows the results of methioninase activity in attenuated *Salmonella*.

Mix L-methionine and pyridoxal with VNP20009, VNP20009-V and VNP20009-M respectively, incubate at 37° C. for 10 min, and then terminate by 50% TCA, centrifuge to get the supernatant and fully mix with MBTH. After incubation at 50° C. for 30 min, measure the absorbance at 320 nm (the amount of enzyme that catalyzes and converts 1 µmol α-Ketobutyric acid per min is defined as one enzyme activity unit). Results are shown in FIG. 3. The methioninase activity of *Salmonella* VNP20009-M is 10 times higher than that of VNP20009 and VNP20009-V.

Example 2

The Anti-Tumor Effect of VNP20009 and its Genetically Engineered Bacterium

1. Culture androgen-independent prostate cancer cell PC-3 using F-12K medium containing 10% fetal bovine serum and inoculate $2 \times 10^6$ cells on the right armpit of nude mice. Observe the state of mice every 2 to 3 days and measure the tumor size using a vernier caliper (volume=$0.52 \times length \times width^2$). When the tumor size reaches 0.1~0.2 cm$^3$, tumor-bearing mice are randomized: PBS control, VNP20009, VNP20009-V and VNP20009-M groups.

Figure 4:
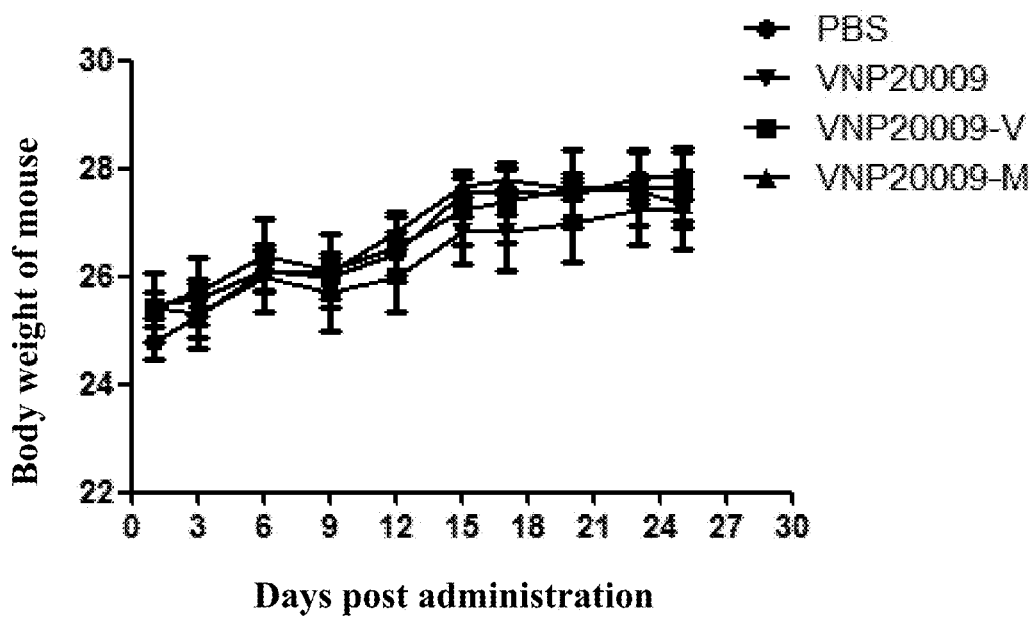
FIG. 4 shows the influence of *Salmonella* injection on the body weight of nude mice.

2. Culture VNP20009, VNP20009-V and VNP20009-M with LB-O. When OD≈0.6, collect the thallus and resuspend it in PBS. Mice are administered by intratumoral injection at a dose of $2 \times 10^6$ CFU each while the control group are administered with the same volume of PBS. After administration, observe the activities, eating Patterns and body weight of nude mice, results are shown in FIG. 4. After bacterial injection, the body weight of mice is not affected; moreover, the feeding and feces of nude mice have no abnormalities, indicating that VNP20009, VNP20009-V and VNP20009-M have no obvious toxicity to nude mice.

Figure 5:
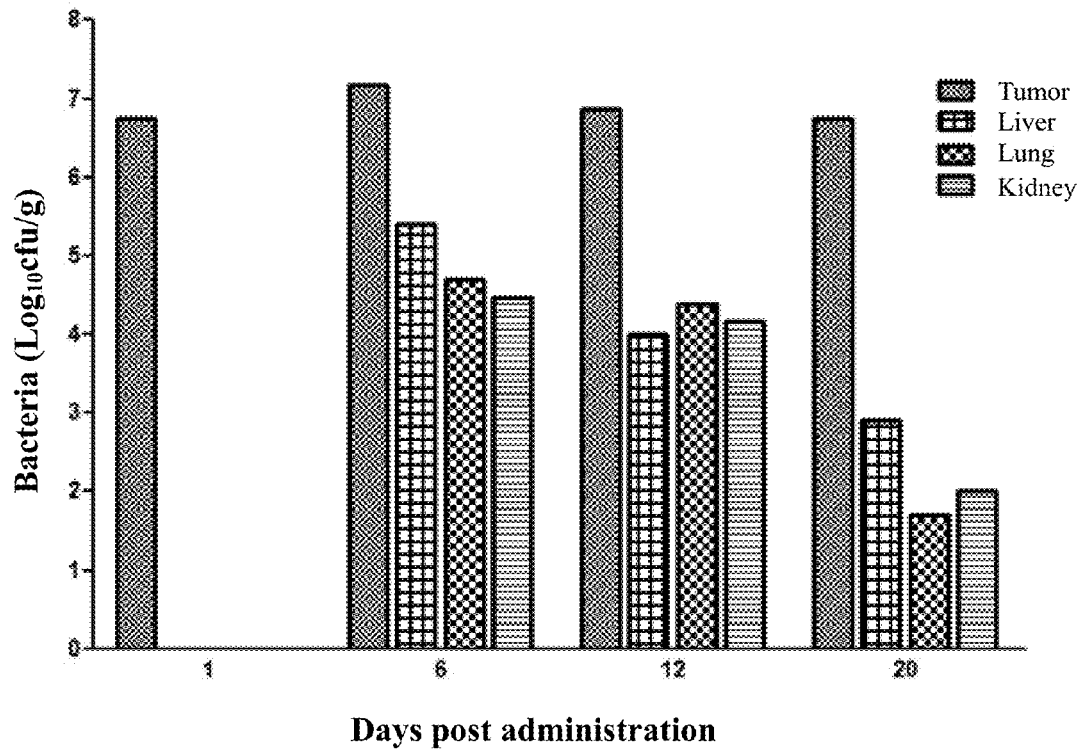
FIG. 5 shows the results of *Salmonella* distribution following intratumoral injection in nude mice.

3. On day 1, 6, 12, 20 post administration, take the major tissues of nude mice, grind and homogenize with PBS and culture them on LB plates overnight after gradient dilution. Results are shown in FIG. 5—the quantitative colony count results of tissue homogenate. After one day of intratumoral bacteria injection, the bacteria count in the tumor tissue is $3.5 \times 10^7$ CFU/g, while no bacteria is detected in liver, kidney, etc. Twelve days later, the count of bacteria in the tumor tissue is $7.5 \times 10^7$ CFU/g, while that in the liver is $1 \times 10^5$ CFU/g, to reach a ratio about 750:1. Twenty days later, the ratio of bacteria between the tumor tissue and other tissues is about 6900:1≈1000:1, indicating that VNP20009 has a well targeting ability to this kind of prostate tumor.

Figure 6:
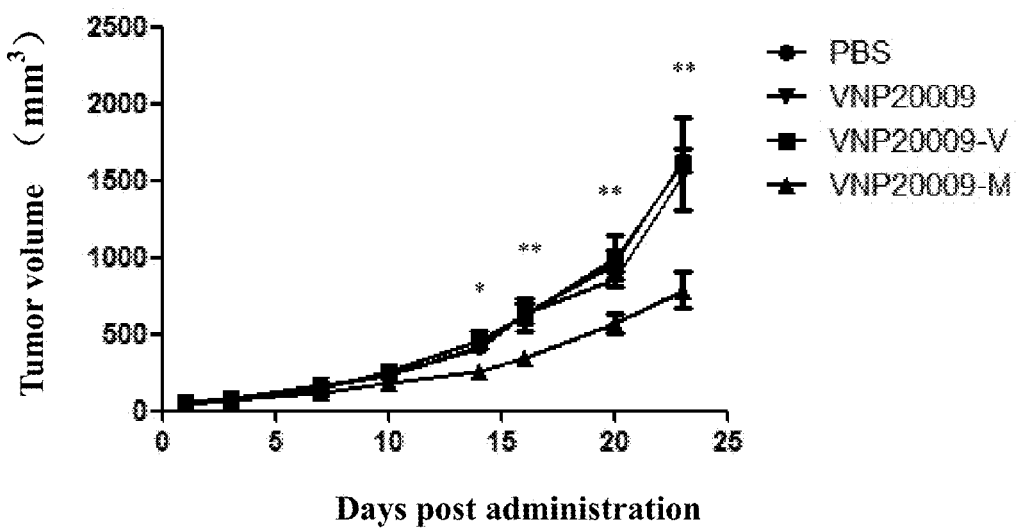
FIG. 6 shows the curve of tumor volume change after administion of $2\times10^4$ CFU *Salmonella*.
Figure 7:
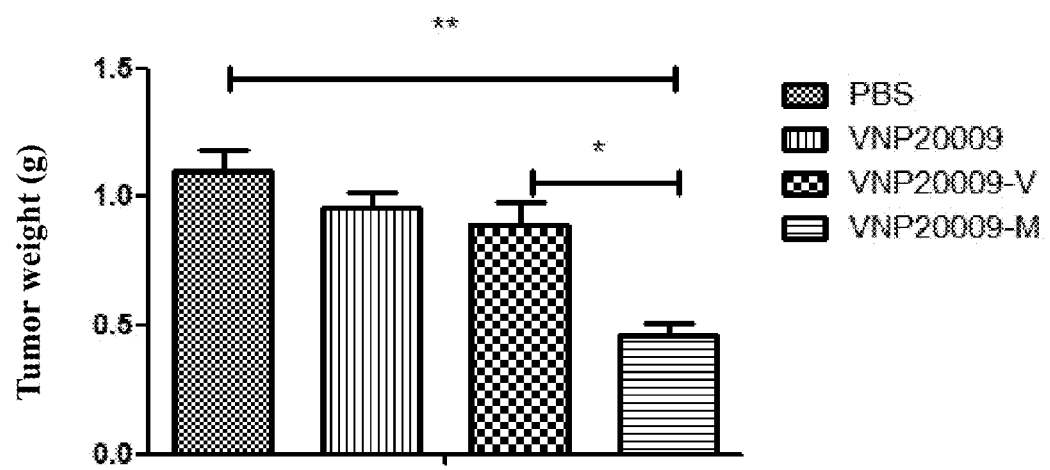
FIG. 7 shows the tumor weight 3 weeks after administration of $2\times10^4$ CFU *Salmonella*.
Figure 8:
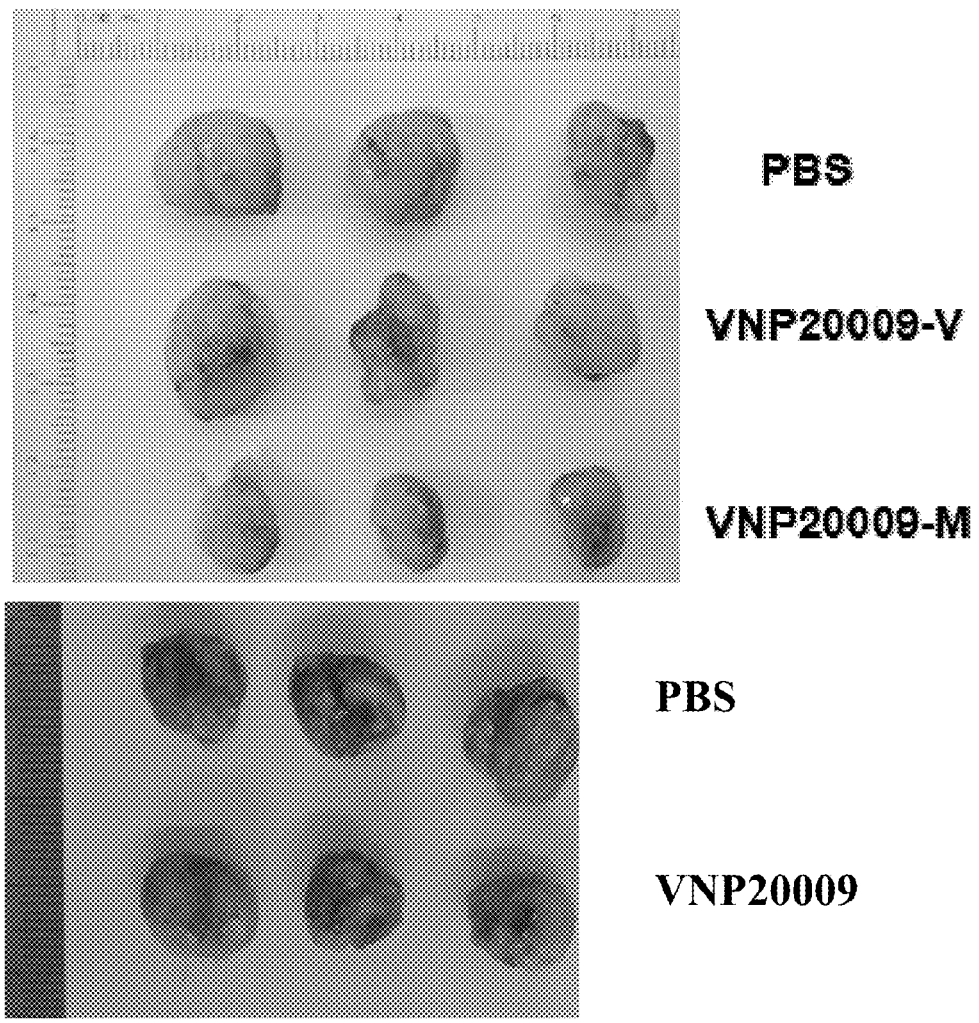
FIG. 8 shows the tumor size 3 weeks after administration of $2\times10^4$ CFU *Salmonella*.

4. The procedures are the same as those in 1, 2. The experimenting dose of *Salmonella* is $2 \times 10^4$ CFU/mouse, that is, the low-dose group. After administration, measure the length and width of the tumor every 2-3 days, calculate the tumor volume and plot the tumor volume curve of nude mice (FIG. 6). Three weeks after administration, randomly take three mice from the control and the test groups, strip the tumor of the nude mice, weigh it and take photos (FIG. 7-8). The results are shown in FIG. 6, after administration with $2 \times 10^4$ CFU *Salmonella* VNP20009-M, the tumor volume and weight is about ½ of that in the PBS group. Nevertheless, administration of the same amount of VNP20009, VNP20009-V show no significant tumor inhibitory effect, suggesting that the inhibitory effect of *Salmonella* VNP20009-M was significant on this kind of prostate cancer.

Figure 9:
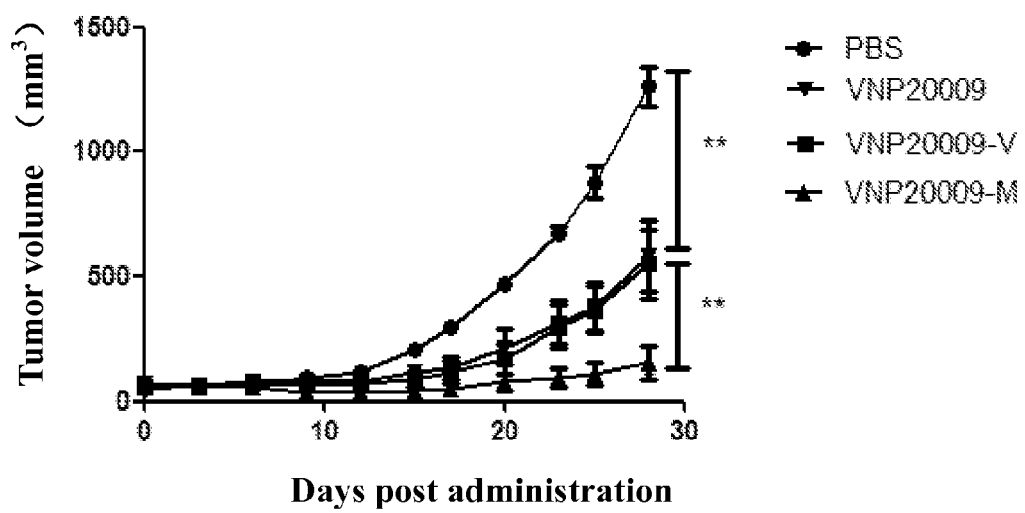
FIG. 9 shows the curve of tumor volume change after administration of $2\times10^6$ CFU *Salmonella*.
Figure 10:
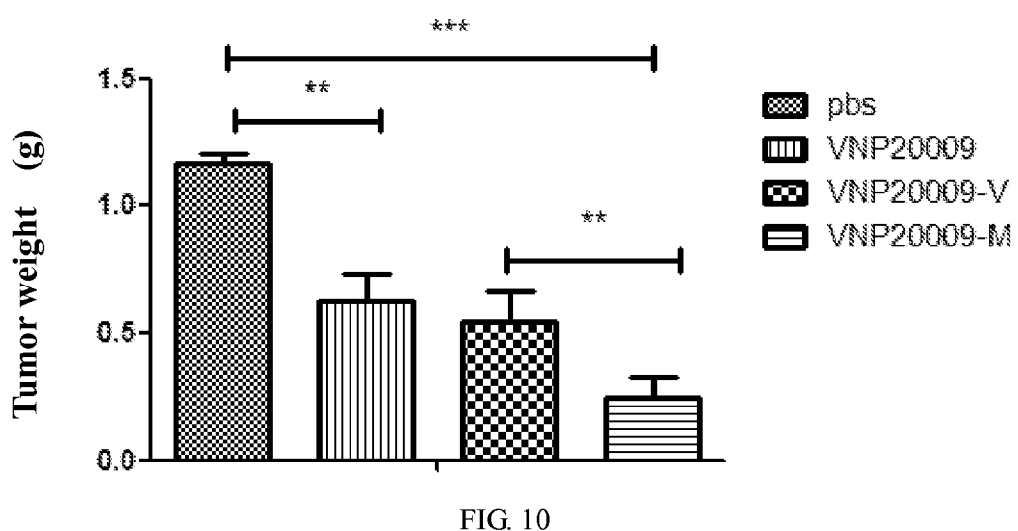
FIG. 10 shows the tumor weight 3 weeks after administration of $2\times10^6$ CFU *Salmonella*.
Figure 11:
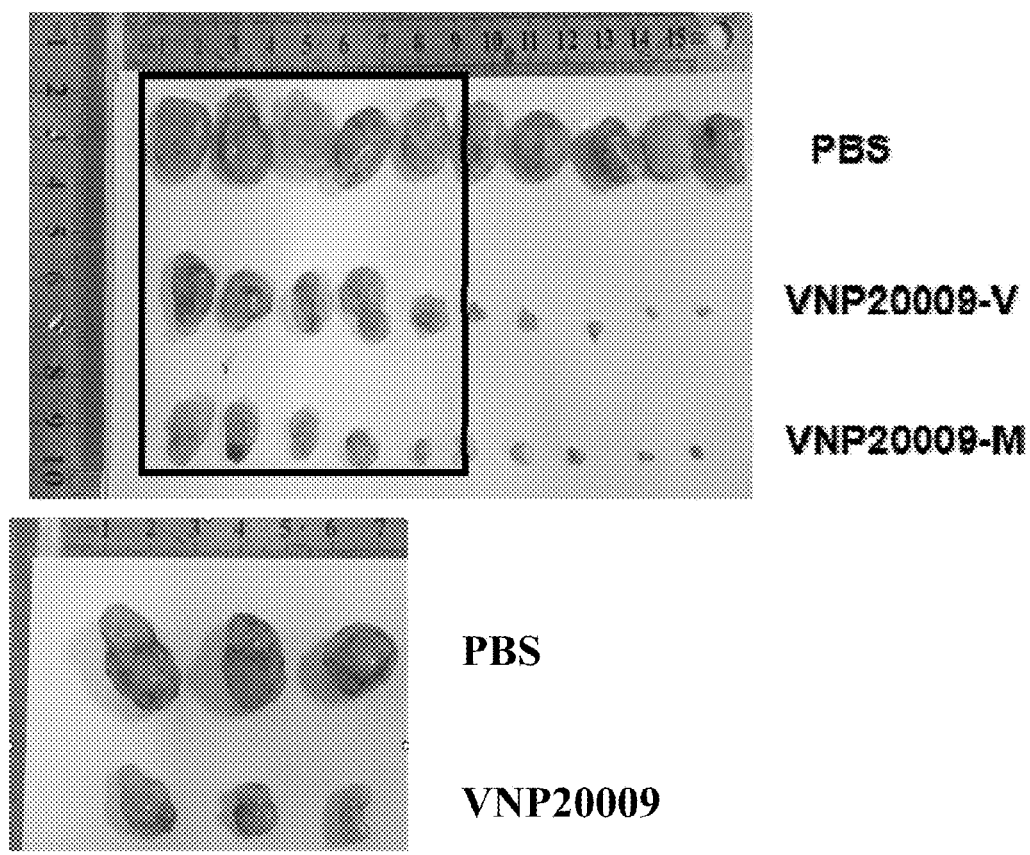
FIG. 11 shows the tumor size 3 weeks after administration of $2\times10^6$ CFU *Salmonella*.
Figure 12:
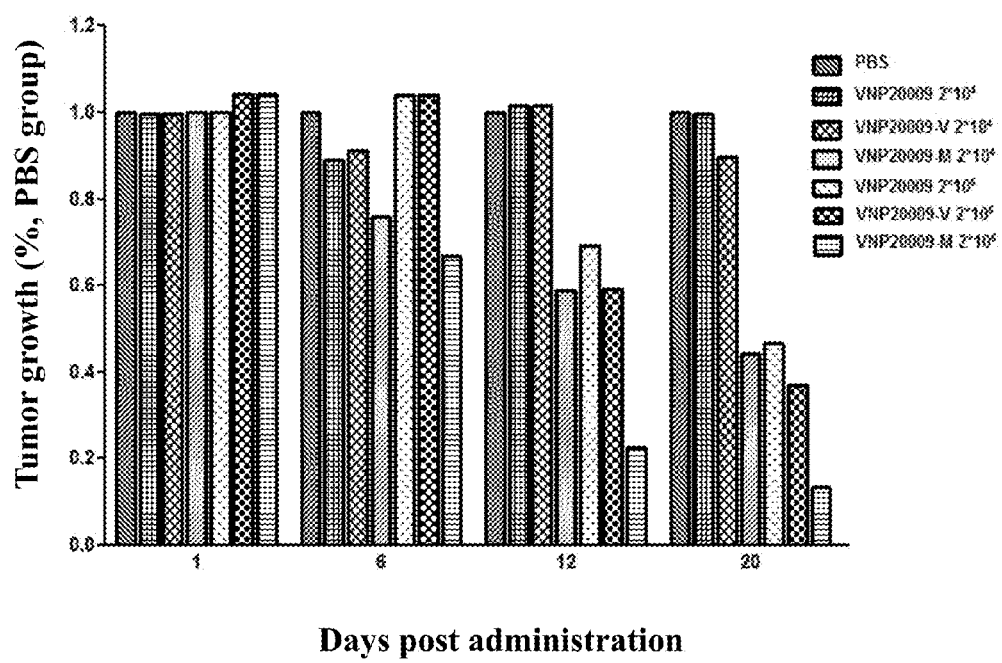
FIG. 12 shows the relative percentage of tumor volume to PBS-treated group after administration of $2\times10^4$ CFU, $2\times10^6$ CFU, *Salmonella* respectively.
Figure 13:
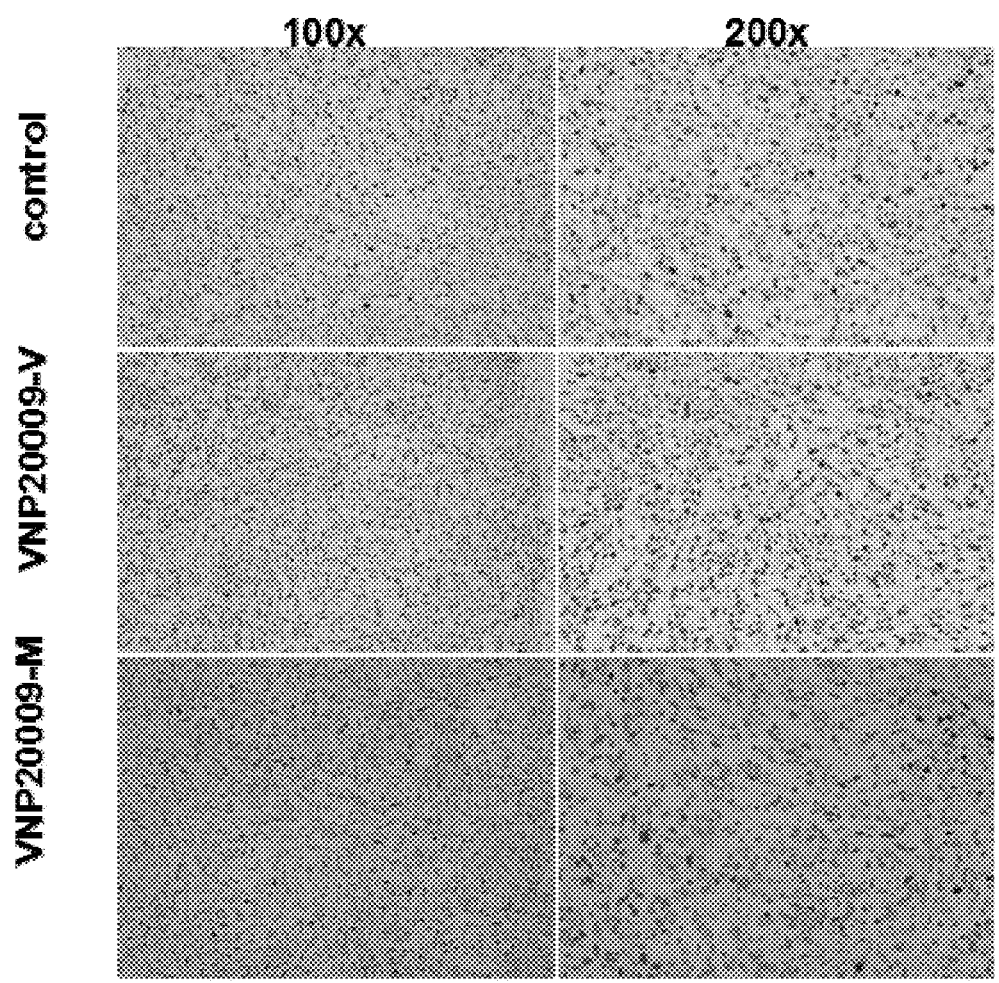
FIG. 13 shows the staining of tumor proliferation antigen ki67 in tumor tissue 4 weeks after staining $2\times10^6$ CFU *Salmonella*.

5. The procedures are the same as those in 1, 2, and 4. The dosage of *Salmonella* is increased to $2 \times 10^6$ CFU/mouse (high-dose group). Results are shown in FIG. 9. After administered with *Salmonella* VNP20009 or VNP20009-V, the tumor grows slowly and the volume and weight are about ⅓ of those in the PBS control group. After administered with *Salmonella* VNP20009-M, the tumor growth mostly arrests in most mice, the tumor volume and weight (FIG. 10,11) are about ½ of those in VNP20009, VNP20009-V group, and ¼ of those in PBS control group. Four weeks after administration, take the tumor tissues to fix with 4% formalin overnight, and the paraffin-embedded sections are stained with tumor proliferation antigen ki67. Immunohistochemical results (FIG. 13) show that in VNP20009-M tumor tissues positive staining rate of ki67 is lower than that in the PBS control and VNP20009-V groups, suggesting that cell proliferation is reduced. By comprehensive comparison of the anti-tumor effects of different doses of VNP20009, VNP20009-V and VNP200009-M (FIG. 12), results show that, the anti-tumor effect is significantly enhanced with the increasing of bacteria dose. VNP20009 and VNP20009-V show similar anti-tumor effect at the same dose without significant difference. Low dose of VNP20009 or VNP200009-V shows no significant anti-tumor effect, while low dose of VNP20009-M can significantly inhibit the tumor growth. However, with the enhancing of the *Salmonella* injection dose, significant anti-tumor effects are shown in all groups, especially in VNP200009-M, the anti-tumor growth rate is close to 90% on the 3rd week. These results suggest that all the *Salmonella* VNP20009, VNP20009-V and VNP20009-M can inhibit the proliferation of the prostate cancer cells, thereby inhibiting tumor growth.

All these results indicate that our attenuated *Salmonella typhimurium* used herein not only has good anti-tumor effect, but also can target to the tumor sites and multiply.

The present invention shows that attenuated *Salmonella typhimurium* has tumor targeting and significant inhibitory effect on prostate cancer cells. Meanwhile, its genetically engineered bacterium constructed with plasmid also has the tumor targeting ability, what's more, attenuated *Salmonella typhimurium* with L-methioninase gene-cloned plasmid can continuously express L-methioninase in the tumor tissues, consuming a significant amount of methionine and other nutrients, which makes the cells of tumor tissue lack of nutrition and grow slowly. Thus, it can be used to preparing the drugs for the treatment of prostate cancer. Wherein, the said plasmid is pSVSPORT plasmid, pTrc99A plasmid, pcDNA3.1 plasmid, pBR322 plasmid, and pET23a plasmid and the above plasmids with cloned L-methioninase gene also have similar anti-tumor effects.

The invention claimed is:

1. An application of a genetically engineered bacterium in preparing drugs for the treatment of prostate cancer, wherein said genetically engineered bacterium is recombinant attenuated *Salmonella typhimurium* VNP20009 carrying plasmid from the group consisting of pSVSPORT plasmid, pTrc99A plasmid, pcDNA3.1 plasmid, pBR322 plasmid or pET23a plasmid, and the said plasmid carries the L-methioninase gene.

2. The application according to claim 1, wherein procedures for the construction of said genetically engineered bacterium are as follows: the L-methioninase gene is subcloned into the plasmid to obtain L-methioninase expression plasmid, and the L-methioninase expression plasmid is transformed into attenuated *Salmonella typhimurium* VNP20009, to obtain the genetically engineered bacterium.

3. The application according to claim 2, wherein said electroporation condition is as follows: voltage 2400V, resistance 400Ω, capacitance 25 µF, discharge time 4 ms.

4. The application according to claim 2, wherein when pSVSPORT plasmid is used in the construction of genetically engineered bacterium, the L-methioninase gene is subcloned into the plasmid through the Kpn I and Hind III restriction sites to obtain L-methioninase expression plasmid, which then is transformed into attenuated *Salmonella typhimurium* VNP20009, to get the genetically engineered bacterium.

5. The application according to claim 1, wherein a route of administration is intratumoral injection.

\* \* \* \* \*